(12) United States Patent
Okano

(10) Patent No.: US 6,600,020 B1
(45) Date of Patent: Jul. 29, 2003

(54) CANINE INTERLEUKIN 18 POLYPEPTIDE

(75) Inventor: Fumiyoshi Okano, Nagoya (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 09/445,724

(22) PCT Filed: Aug. 7, 1998

(86) PCT No.: PCT/JP98/03524
§ 371 (c)(1),
(2), (4) Date: Dec. 13, 1999

(87) PCT Pub. No.: WO99/07851
PCT Pub. Date: Feb. 18, 1999

(30) Foreign Application Priority Data

Aug. 7, 1997 (JP) ............................................. 09-213754

(51) Int. Cl.[7] .......................... C07K 14/54; C12N 5/10; C12N 15/24; C12N 15/63

(52) U.S. Cl. ................... 530/351; 435/69.52; 435/71.1; 435/71.2; 435/471; 435/325; 435/320.1; 435/252.3; 435/254.11

(58) Field of Search ....................... 530/351; 435/69.52, 435/71.1, 71.2, 471, 325, 320.1, 252.3, 254.11

(56) References Cited

PUBLICATIONS

Shimpei Ushio et al : The Journal of Immunology 1996 156, 4274–4279, "Cloning of the cDNA for Human...".

Haruki Okamura et al : Nature vol. 378 Nov. 1995, pp. 88–91, "Cloning of a new cytokine that induces...".

*Primary Examiner*—Prema Mertz
(74) *Attorney, Agent, or Firm*—Nixon & Vanderhye, P.C.

(57) ABSTRACT

The present invention relates to canine interleukin 18 and an interleukin 18 production method.

2 Claims, No Drawings

CANINE INTERLEUKIN 18 POLYPEPTIDE

TECHNICAL FIELD

The present invention relates to recombinant vectors, recombinant viruses, transformants, canine interleukin 18, canine interleukin 1β converting enzyme and interleukin 18 production methods, where the objective is to mass produce by genetic manipulation.techniques canine interleukin 18 the protein primary structure of which is derived from canine genetic information and to thus make pharmaceuticals for animal use (antitumour drugs/anti-allergy drugs/antiviral drugs/vaccine adjuvants).

TECHNICAL BACKGROUND

Interleukin 12 (hereinafter abbreviated to IL12), which shows immune control action, is a cytokine which possesses actions comprising interferon γ inducing activity and physiological activity in regard to, for example, activating natural killer cells and type 1 helper T cells (reference 1) and, in particular, as a result of a powerful activating action in respect of cellular immunity, it is regarded as having very good prospects as an antitumour drug and anti-allergy drug candidate (references 2 and 3). Interleukin 18 (hereinafter abbreviated to IL18) has also been recently cloned as a cytokine showing the same kind of activity as IL12 (reference 4), and it has been reported that due to synergistic action with IL12 the activities thereof are further increased (reference 5).

Following mouse IL18 (reference 4), human IL18 cDNA has also been cloned (reference 6) by genetic manipulation techniques, and mass production using these gene recombination techniques has been investigated. However, IL18 does not have a signal sequence required for secretion from within cells. Hence, in order to be secreted from within cells in the active form, processing of an IL18 precursor protein by means of an interleukin 1β converting enzyme (hereinafter abbreviated to ICE) is necessary and so, when the IL18 gene is introduced on its own into animal cells, it is not expressed as the active form of IL18 (reference 7) and therefore the efficient mass production of recombinant form IL18 using cells has been difficult.

Development as remedies for tumours, allergies and viral diseases, etc, may be expected by means of mass production using IL18 gene recombination techniques.

In pets, particularly dogs, in common with humans, there are known many tumours such as mammary gland tumours, allergic dermatitis, and numerous viral diseases such as parvovirus infection and distemper infection, and the development of remedies for these is desired.

The cloning of canine IL18 has not yet been reported. Hence, if canine IL18 could be cloned, it is possible that it could form a novel canine remedy.

Again, if it were possible to readily mass produce IL18 in cells using gene recombination techniques, then there could be expected to emerge L18 applications as, for example, human and animal antitumour drugs, anti-allergy drugs and antiviral drugs, etc.

Against this background, with the objective of cloning canine IL18 cDNA and large-scale expression of the IL18 gene, and based on an original concept, the present inventors have succeeded in cloning the gene coding for canine IL18 from canine cDNA, and furthermore they have produced a recombinant baculovirus containing DNA coding for an IL18 precursor protein, and it has been discovered that by infecting insect cells or larvae with this, surprisingly, the active form of IL18 is produced without ICE treatment, and it has been further discovered that by producing a gene in which there is added the gene coding for the signal sequence in front of the gene coding for the active form of canine IL18, the level of production of the active form of IL18 is further enhanced. Furthermore, the gene coding for canine ICE has been successfully cloned from canine cDNA and a recombinant baculovirus containing at the same time DNA coding for a canine IL18 precursor protein and DNA coding for canine ICE has been produced, and canine IL18 has been successfully mass produced by infecting insect cells or larvae, and hence a method for producing IL18 simply and on a large scale has been established. The present invention has been perfected based on these discoveries.

DISCLOSURE OF THE INVENTION

Specifically, the present invention relates to canine interleukin 18 having at least one of the abilities selected from an ability to act on canine leukocytes and induce antiviral active factors and factors which enhance class II MHC expression on canine tumour cells; an ability to promote the proliferation of canine lymphocytes; an ability to enhance Fas ligand expression on canine lymphocytes and canine tumour cells; an ability to obstruct and destroy canine tumour cells; an ability to bring about a reduction in size of tumours occurring in the bodies of dogs; and an ability to activate canine leukocytes and suppress canine allergies.

Furthermore, the present invention offers recombinant vectors which bring about the production of IL18, *Escherichia coli* transformants possessing these recombinant vectors, recombinant baculoviruses which bring about the production of IL18 in insect cells or larvae, IL18 obtained therefrom, and also an IL18 production method. Moreover, the present invention also offers a gene coding for canine IL18, canine ICE and a gene coding for canine ICE. Furthermore, it offers a canine immune disease remedy containing IL18.

OPTIMUM FORM FOR PRACTISING THE INVENTION

A recombinant vector in which there has been inserted DNA coding for canine IL18 of the present invention can be produced, for example, as follows. After extracting poly (A) RNA from canine cells, cDNA synthesis is carried out and, using primers based on the gene sequences coding for mouse or human IL18, polymerase chain reactions (hereinafter abbreviated to PCR) are conducted.

Furthermore, from the synthesized cDNA a phage library is produced and, by carrying out plaque hybridization with the gene fragments obtained by PCR, full length canine IL18 cDNA can be cloned. Full length canine ICE cDNA can be cloned similarly.

As methods for obtaining RNA from canine organs and the like, there are the usual methods such as, for example, those employing polysome isolation, sucrose density gradient centrifugation and electrophoresis. The extraction of the RNA from the aforesaid canine organs and canine cells can be carried out by selection of a suitable method from amongst the guanidine thiocyanate-cesium chloride method where guanidine thiocyanate treatment is carried out followed by CsCl density gradient centrifugation (reference 8), the method of phenol extraction following treatment with a surfactant in the presence of a ribonuclease inhibitor, using a vanadium complex (reference 9), the guanidine thiocyanate-hot phenol method, the guanidine thiocyanate-guanidine hydrochloride method, the guanidine thiocyanate-phenol chloroform method, and the method where treatment with guanidine thiocyanate is carried out followed by treatment with lithium chloride, and RNA precipitation effected.

From canine organs and, for example, mitogen-stimulated canine monocytes and lymphocytes, mRNA is isolated by the usual methods, for example the lithium chloride/urea method, the guanidine isothiocyanate method and the oligo dT cellulose column method, etc, and cDNA is synthesized from the mRNA obtained by the usual methods, for example by the method of Gubler et al. (reference 10) or the method of H. Okayama et al. (reference 11). To synthesize cDNA from the mRNA obtained, basically besides using avian myeloblastosis viral (AMV) or other such reverse transcriptase, there may be combined methods where DNA polymerase or the like is employed using partial primers. The use of commercial synthesis or cloning kits is convenient.

Using this cDNA as a template, PCR is carried out using primers based on mouse or human base sequences and furthermore, after ligating the synthesized cDNA to a γ phage vector, packaging is carried out by mixing in vitro with γ phage coat protein, etc, and the *E. coli* which constitutes the host is infected with these created phage particles. In such circumstances, γ phage-infected *E. coli* undergoes lysis and individual clones are recovered as plaques. These plaques are transferred to nitrocellulose or other such filters and, by hybridization using as probes radioactively labelled genes obtained by PCR, the canine IL18 and canine ICE can be cloned.

Procaryotes or eucaryotes can be used as the hosts. As procaryotes, there can be used bacteria, in particular *Escherichia coli* and bacteria of the genus Bacillus, for example *Bacillus subtilis*, etc. As eucaryotes, there can be used eucaryotic microorganisms such as yeasts, for example yeasts of the genus Saccharomyces, e.g. *Saccharomyces serevisiae* or the like, insect cells, for example *Spodoptera frugiperda* cells, Trichoplusiani cells and *Bombyx mori* cells, and animal cells, for example human cells, monkey cells, mouse cells and the like. In the present invention, there can furthermore be used the organisms themselves, for example insects such as *Bombyx mori*, Trichoplusiani and the like.

As expression vectors, there can be used plasmids, phages, phagemids and viruses (baculo (insect), vaccinia (animal cells), etc). Promoters within the expression vectors are selected depending on the host, for example as promoters for bacteria, the lac promoter, trp promoter and the like, can be used and, as promoters for yeasts, for example the adh1 promoter, pak promoter and the like, can be used. Furthermore, as promoters for insects, there are the baculovirus polyhedrin promoter and the p10 promoter, and for animal cells there are the simian virus 40 early or late promoter, and the like, but there is no restriction thereto.

Host transformation by means of the expression vectors can be carried out by conventional procedures well known to those skilled in the art. These methods are described in, for example, Current Protocols in Molecular Biology, published by John Wiley & Sons. Culture of the transformants can also be carried out in accordance with conventional procedure.

When IL18 is produced using cells, because the signal sequence is not present in the precursor protein, IL18 precursor protein processing by means of ICE or the like, is necessary. Consequently, by simultaneously bringing about expression in terms of the IL18 precursor protein and ICE, the active form of IL18 can be produced. For example, by using an expression vector simultaneously containing the gene coding for canine IL18 and the gene coding for canine ICE shown in Sequence No: 2, the active form of canine IL18 can be produced in cells.

Furthermore, by adding a gene coding for the signal sequence in front of the gene coding for the active form of IL18, the active form of IL18 can be produced. For example, by using a gene containing the gene coding for the signal sequence as shown in Sequence No: 9, the active form of canine IL18 can be produced in cells.

Canine IL18 can be produced using a *Bombyx mori* expression system, for example by producing recombinant *Bombyx mori* nuclear polyhedrosis virus which infects *Bombyx mori*. The recombinant *Bombyx mori* nuclear polyhedrosis virus can be produced by cotransfecting a *Bombyx mori* established cell line with a recombinant plasmid produced by ligating DNA coding for the canine IL18 protein in a *Bombyx mori* cloning vector and *Bombyx mori* nuclear polyhedrosis viral DNA. Hence, the recombinant virus can be produced by an in vivo method.

Specifically, there can be produced a recombinant plasmid in accordance with normal genetic manipulation where the DNA portion coding for the canine IL18 protein is ligated downstream of the expression control portion of a *Bombyx mori* cloning vector such as, for example, pBK283. After cotransfecting a *Bombyx mori* established cell line, for example BM-N strain (reference 12), by methods such as those in the literature with this recombinant plasmid and *Bombyx mori* nuclear polyhedrosis viral DNA (reference 12), culture is continued and the recombinant virus can be cloned from amongst the non-recombinant (wild type) and recombinant viruses appearing in the culture fluid by the usual methods such as the limiting dilution method or the plaque method. Since the recombinant virus does not have a polyhedrin forming capability, it can be readily distinguished from the wild type virus. The production of canine IL18 is carried out by bringing about the proliferation of the aforementioned recombinant *Bombyx mori* nuclear polyhedrosis virus within a *Bombyx mori* established cell line or within *Bombyx mori* organisms.

When a *Bombyx mori* established cell line is used, BM-N cells are infected using culture fluid containing the aforementioned-recombinant virus and cultured by attached culture or suspension culture. For the culture medium used to culture the BM-N cells there can be used, for example, TC-10 medium to which bovine serum has been added (reference 12). Regarding the culture temperature, 25–28° C. is suitable. After culture, the culture fluid is centrifuged and the canine IL18 is recovered from the supernatant.

When *Bombyx mori* organisms are used, culture fluid containing the aforementioned recombinant virus is injected into *Bombyx mori* larvae, synthetic feed is given and rearing carried out. After rearing, the body fluid is collected and canine IL18 is recovered from the supernatant thereof.

When determined by sodium dodecyl sulphate-polyacrylamide gel electrophoresis (SDS-PAGE) under non-reducing conditions, the apparent molecular weight of the canine IL18 protein produced is approximately 15–20 kD.

As shown in the following examples, the canine IL18 is characterized by activities such as a capacity for inducing canine IFN γ from canine leukocytes, an expression enhancing capacity in respect of Fas ligand molecules on tumour cells and an antitumour action in respect of canine tumour cells. Canine IFN γ activity is measured on the basis of antiviral activity using the CPE method (reference 14) and expression enhancing activity in respect of class II MHC molecules on canine tumour cells. Regarding the expression enhancing activity in respect of Fas ligand molecules and the expression enhancing activity in respect of class II MHC molecules on tumour cells, fluorescence labelled antibodies to these molecules are reacted with the cells and the intensity of fluorescence is measured by means of a device for measuring fluorescence intensity such as a flow cytometer, and activity can be judged to exist if this increases by 10% or more.

EXAMPLES

Below, the present invention is explained in further detail by providing examples.

Example 1

Canine IL18 Cloning (1) Preparation of Canine cDNA

Total RNA was prepared using ISOGEN (produced by the Nippon Gene Co.) from canine pancreas, kidney, liver and lymphocytes derived from canine spleen treated for 7 hours with avian Newcastle disease virus. The RNA obtained was dissolved in 10 mM Tris-HCl buffer solution (pH 7.5) containing 1 mM EDTA (hereinafter abbreviated to TE) and, after treatment at 70° C. for 5 minutes, an equal amount of TE containing 1 M LiCl was added. The RNA solution was applied to an oligo dT cellulose column which had been equilibrated with TE containing 0.5 M LiCl and washing with the same buffer solution was carried out. After further washing with TE containing 0.3 M LiCl, the adsorbed poly (A) RNA was eluted with 2 mM EDTA (pH 7.0) containing 0.01% SDS. Using the poly (A) RNA thus obtained, single-stranded cDNA was synthesized. Specifically, 5 µg of poly (A) RNA and 0.5 µg of oligo dT primer (12–18 mer) were introduced into a sterilized 0.5 ml microcentrifuge tube, then made up to 12 µl by adding diethyl pyrocarbonate-treated sterile water and, after incubating at 70° C. for 10 minutes, immersed in ice for 1 minute. To this, 200 mM Tris-HCl (pH 8.4), 2 µl of 500 mM KCl solution, 2 µl of 25 mM MgCl$_2$, 1 µl of 10 mM dNTP and 2 µl of 0.1 M DTT were respectively added and, after incubating at 42° C. for 5 minutes, there was added 1 µl comprising 200 units of SuperScript II RT produced by Gibco BRL. Then, incubation was carried out at 42° C. for a further 50 minutes, and the cDNA synthesis reaction was performed. Incubation was further carried out at 70° C. for 15 minutes, the reaction terminated, and placed on ice for 5 minutes. To this reaction fluid was added 1 µl of *E. coli* RNaseH (2 units/ml) and incubation carried out at 37° C. for 20 minutes.

(2) Preparation of a Canine cDNA Phage Library

Using 1 µg quantities of the aforementioned poly (A) RNA obtained in (1), by means of a Pharmacia TimeSaver cDNA synthesizing kit and in accordance with the accompanying manual, double-stranded cDNA was synthesized using oligo dT primers and furthermore EcoRI/NotI adapters were ligated. Using the product, by means of an Amersham cDNA rapid cloning module-λgt10 and in accordance with the accompanying manual, recombinant λgt10 vectors were prepared and, furthermore, by means of an Amersham in vitro packaging module and in accordance with the accompanying manual, recombinant phages were prepared.

(3) Canine IL18 cDNA Cloning

On the basis of the mouse IL18 base sequence (reference 4), the two primer types:

5' aactttggccgacttcactgtacaaccgcagtaatacgga 3' (SEQ ID NO:9) and

5' ccttcatacagtgaagattcaaactccatcttgttgtgtc 3' (SEQ ID NO:10)

were synthesized using a DNA synthesizer. Into a 0.5 ml microcentrifuge tube there was placed 2 µl of the aforementioned cDNA obtained from canine liver in (1) and to this was added 20 pmol of each primer and various reagents so as to give a 20 mM Tris-HCl buffer solution (pH 8.0), 1.5 mM MgCl$_2$, 25 mM KCl, 100 µg/ml gelatin, 50 µM of each dNTP and 4 units of Taq DNA polymerase, the whole being made up to a volume of 100 µl. Using an MJ Research Programmable Thermal Controller under respective 35 conditions comprising DNA denaturation conditions of 94° C. for 1 minute, primer annealing conditions of 45° C. for 2 minutes and primer extension conditions of 72° C. for 3 minutes, 40 cycles of reaction were effected. The product was subjected to electrophoresis using 1% agarose gel and an approximately 360 bp DNA fragment was prepared in accordance with normal procedure (reference 13).

This DNA fragment was ligated to an Invitrogen T-Vector using a Takara Shuzo Co. DNA Ligation Kit Ver. 2. Then employing this, *E. coli* was transformed in accordance with conventional procedure and, from the transformants obtained, plasmid DNA was prepared by the usual method. Next, it was confirmed by PCR under the same conditions as aforementioned that the plasmid had a PCR fragment inserted and, using a fluorescent DNA sequencer (DNA Sequencer 373S produced by Perkin Elmer) and in accordance with the accompanying protocol, using a Perkin Elmer Dye Terminator Cycle Sequencing Kit the base sequence of the inserted DNA was determined. Next, using a Takara Shuzo Co. Random Primer DNA Labelling Kit, the 360 bp DNA fragment containing this sequence was labelled with $^{32}$P and a probe produced. The aforementioned recombinant phage library prepared from canine liver cDNA obtained in (2) was formed as plaques on *E. coli* NM514 and transfer effected in accordance with normal procedure to Amersham Hybond-N+. The Hybond-N+ was incubated at 65° C. for 2 hours in 5×SSPE (0.9 M NaCl, 50 mM NaH$_2$PO$_4$, 5 mM EDTA, pH 7.4), 5×Denhardt solution (0.1% Ficoll, 0.1% polyvinyl pyrrolidone and 0.1% bovine serum albumin), 0.1% SDS and 100 µg/ml salmon sperm DNA, and then hybridization was carried out with 1×10$^6$ cpm/ml of labelled probe prepared as aforementioned in the same solution. After incubation at 65° C. overnight, the Hybond-N+ was washed 3 times for 15 minutes in 0.2×SSC (30 mM NaCl and 3 mM sodium citrate) and 0.1% SDS, exposed for 12 hours to a Fuji Photo Film Co. Fuji Imaging Plate and analyzed using a Fuji Photo Film Co. Bioimaging Analyzer. Plaques having positive signals were subjected to re-screening in accordance with conventional procedure. As a result of screening three times, one recombinant phage with a positive signal was obtained. From this recombinant phage, the phage DNA was extracted in accordance with normal procedure and, after cleavage with restriction enzyme EcoRI, an approximately 1.4 kb DNA fragment obtained by 1% agarose gel electrophoresis was prepared in accordance with normal procedure and then ligated to Takara Shuzo Co. pUC118BAP-treated DNA (EcoRI/BAP) using Takara Shuzo Co. DNA Ligation Kit Ver. 2. Using this, plasmid DNA was prepared in the normal way and, using a fluorescent DNA sequencer (DNA Sequencer 373S produced by Perkin Elmer) and, in accordance with the accompanying protocol, using a Perkin Elmer Dye Terminator Cycle Sequencing Kit, the base sequence of the approximately 1.4 kb DNA fragment obtained was determined. Within this, the sequence coding for the canine IL18 precursor is shown in Sequence No: 1 and the total base sequence is shown in Sequence No: 3.

(4) Canine ICE cDNA Cloning

On the basis of the human ICE base sequence (reference 15), the two primer-types:

5' atggccgacaaggtcctgaaggagaagagaaagctgttt 3' (SEQ ID. NO: 11) and

5' atgtcctgggaagaggtagaaacatcttgtcaaagtcac 3' (SEQ ID NO:12)

were synthesized using a DNA synthesizer. Into a 0.5 ml microcentrifuge tube there was placed 2 μl of the aforementioned cDNA obtained from lymphocytes derived from canine spleen treated with avian Newcastle disease virus in (1) and to this was added 20 pmol of each primer and various reagents so as to give a 20 mM Tris-HCl buffer solution (pH 8.0), 1.5 mM $MgCl_2$, 25 mM KCl, 100 μg/ml gelatin, 50 μM of each dNTP and 4 units of Taq DNA polymerase, the whole being made up to a volume of 100 μl. Using an MJ Research Programmable Thermal Controller under respective conditions comprising DNA denaturation conditions of 94° C. for 1 minute, primer annealing conditions of 55° C. for 2 minutes and primer extension conditions of 72° C. for 3 minutes, 35 cycles of reaction were effected. The product was subjected to electrophoresis using 1% agarose gel and an approximately 1.2 kb DNA fragment was prepared. In the same way as in (3) above, after determining the base sequence of this DNA fragment a labelled probe was prepared using the 1.2 kb DNA fragment containing this sequence. A recombinant phage library prepared from the aforementioned cDNA obtained from lymphocytes derived from canine spleen treated with avian Newcastle disease virus obtained in (2) was hybridized with the aforementioned labelled probe in the same way as in (3) and screening carried out. DNA was extracted from one recombinant phage having a positive signal obtained as a result and, after cleavage with restriction enzyme NotI, an approximately 1.5 kb DNA fragment obtained by 1% agarose gel electrophoresis was ligated, in accordance with normal procedure, to the STRATEGENE pBluescript II NotI site. Using this, plasmid DNA was prepared and, employing a fluorescent DNA sequencer, the base sequence of the approximately 1.5 kb DNA fragment obtained was determined. Within this, the sequence coding for canine ICE is shown in Sequence No:2 and the total base sequence is shown in Sequence No:4.

Example 2

Canine IL18 Production (1) Canine IL18 Production by *E. coli*

Using as a template the DNA coding for the canine IL18 precursor protein obtained in Example 1, and using primers to which restriction enzyme NcoI and BamHI cleavage sites had been added, by means of the PCR method there was prepared a DNA fragment coding for the active form of the canine IL18 protein to which NcoI and BamHI cleavage sites had been added. This DNA fragment was cleaved with restriction enzymes and ligated to restriction enzyme NcoI and BamHI cleavage sites downstream of the promoter of pET8c which is an *E. coli* expression vector. *E. coli* HB101 was transformed using this in accordance with normal procedure. Among the colonies growing on an LB plate containing 100 μg/ml ampicillin, 15 were cultured for 8 hours in 3 ml of LB medium containing 100 μg/ml of ampicillin and plasmids were extracted from the microorganisms collected. After purification, there was obtained a plasmid containing the DNA sequence coding for the active form of canine IL18 from which, on cleavage with restriction enzymes NcoI and BamHI, an approximately 580 bp DNA fragment was obtained. This recombinant vector was designated pETCaIG and, using this, in accordance with the specified procedure, *E. coli* BL21 was transformed. This *E. coli* was named *E. coli* (pETCaIG).

A single colony of the *E. coli* (pETCaIG) obtained was introduced into 5 ml of LB medium containing 100 μg/ml ampicillin. Culture was-carried out at 37° C. until the OD600 reached approximately 0.7 and, after adding isopropyl-β-D-thiogalactopyranoside (IPTG) at a final concentration of 0.5 mM, culturing was carried out for a further 1.5 hours.

In a 1.5 ml microcentrifuge tube, there was placed 1.5 ml of culture fluid and, after centrifuging at 12,000 rpm for 5 minutes, the supernatant was discarded, and the residue suspended in 1.5 ml of 10 mM Tris-HCl (pH 7.5) and the microorganisms were disrupted on ice using a Handy Sonic. Centrifugation was carried out at 20,000 rpm for 30 minutes and a soluble fraction (the supernatant) obtained. Following filtration/sterilization with a 0.22 μm filter, a solution in which canine IL18 had been produced was obtained.

Furthermore, using primers to which the restriction enzyme BamHI cleavage site had been added, by means of the PCR method there was prepared a DNA fragment coding for the active form of the canine IL18 protein to which BamHI cleavage sites had been added and, after restriction enzyme cleavage, ligation was effected to the BamHI cleavage site of pGEX-5X (produced by Pharmacia) which is an *E. coli* expression vector. By the same procedure as above, after transforming *E. coli* BL21, a soluble fraction was obtained. This fraction was applied to a glutathione Sepharose column (produced by Pharmacia). The eluted fraction therefrom was subjected to cleavage using Factor Xa produced by Pharmacia and again applied to the same column. A fraction containing the active form of the canine IL18 protein which did not bind to the column was recovered. On the basis of SDS-PAGE analysis, the purity of the active form of the canine IL18 protein thus purified was 90% or higher. Furthermore, on the basis of analysis using a Wako limulus test kit, there could be detected no endotoxin whatsoever in 1 mg of this protein.

(2) Preparation of Recombinant Baculoviruses for Canine IL18 Production

In accordance with normal procedure, the DNA described in Sequence No: 1 which codes for the canine IL18 precursor was ligated to restriction enzyme PstI and EcoRI cleavage sites downstream of the baculovirus transfer vector pVL1392 (produced by Pharmingen) promoter and a recombinant transfer vector was obtained. Furthermore, using a baculovirus transfection kit produced by Pharmingen, and in accordance with the accompanying manual, recombinant baculovirus rAcCaIG-1 was obtained.

Furthermore, in the same way, the DNA described in Sequence No: 9 which contains a signal sequence was ligated to pVL1392 and a recombinant transfer vector was prepared, and recombinant baculovirus rAcCaIG-2 obtained.

Furthermore, similarly, DNA coding for the canine IL18 precursor and DNA coding for the canine ICE precursor were ligated to restriction enzyme XbaI and BamHI cleavage sites downstream of the baculovirus transfer vector pAcAB3 (produced by Pharmingen) promoter, respectively, and recombinant baculovirus rpAcCaIGICE was obtained.

(3) Canine IL18 Production by Insect Cells

Sf21 cells (derived from Spondoptera frugeruda, produced by Pharmingen) which had been subjected to attached culture until confluent in a 75 $cm^2$ flask using baculovirus Protein Free Insect Medium produced by Pharmingen were infected with the aforementioned rAcCaIG-1, rAcCaIG-2 and rpAcCaIGICE obtained in (2) respectively and, after culturing for 4 days, culture supernatants in which canine IL18 had been produced were obtained.

(4) Preparation of a Recombinant Baculovirus for Canine IL18 Production using *Bombyx mori*

In accordance with normal procedure, the DNA coding for the canine IL18 precursor was ligated to restriction enzyme EcoRI cleavage site downstream of the transfer vector pBK283 (produced by Funakoshi) promoter and a recombinant transfer vector obtained. Recombinant viruses were prepared using the method in reference 12. Thus, into 2.5 ml of a solution consisting of 50 mM HEPES buffer (pH 7.1), 0.28 M NaCl, 0.7 mM $Na_2HPO_4$ and 0.7mM $NaH_2PO_4$, there was added dropwise 2.5 ml of a DNA mixed solution (containing 0.25 M $CaCl_2$, 10 µg of *Bombyx mori* nuclear polyhedrosis virus BmNPV T3 strain (reference 12) DNA and 65 µg of the recombinant transfer vector), and 0.5 ml of the suspension produced was added to the culture medium of approximately $3 \times 10^5$ BmN cells which had been subjected to attached culture in a 25 $cm^2$ flask in 5 ml of TC-10 medium to which 10% FBS had been added (reference 12), and the DNA introduced into the *Bombyx mori* cells. After 20 hours, there was carried out an exchange with fresh medium and, after culturing for a further 7 days, the culture fluid was recovered. This culture fluid was centrifuged and the clarified supernatant was diluted and added to the culture medium of BM-N cells which had been subjected to attached culture. After culturing for 8 days, examination for viral infection was carried out by microscopic observation and the culture medium with which no polyhedra were formed was selected (limiting dilution method).

The limiting dilution method was repeated seven times and recombinant virus rBmCaIG was obtained.

(5) Canine IL18 Production in *Bombyx mori* Organisms

The recombinant virus viral solution obtained in (3) above was injected at a dose of 50 µl/larva into *Bombyx mori* larvae at the 2nd day of the 5th instar stage and, after rearing at 25° C. for 4 days on commercial artificial feed (produced by KANEBO Silk Elegance), the abdomens of 10 of the *Bombyx mori* were cut and the body fluid collected in an ice-cooled Eppendorf tube. After centrifugation, the supernatant was obtained and, following filtration/sterilization using a 0.22 µm filter, there was obtained body fluid in which canine IL18 had been produced.

Example 3

Preparation of Canine IL12

(1) Preparation of Canine IL12 cDNA

Total RNA was prepared using ISOGEN (produced by Nippon 25 Gene Co.) from canine peripheral blood monocytes stimulated for 48 hours with LPS (50 µg/ml). The RNA obtained was dissolved in 10 mM Tris-HCl buffer solution (pH 7.5) containing 1 mM EDTA (this is referred to below as TE) and, after treatment at 70° C. for 5 minutes, an equal amount of TE containing 1 M LiCl was added. The RNA solution was applied to an oligo dT cellulose column which had been equilibrated with TE containing 0.5 M LiCl and then washing with the same buffer solution was carried out. After further washing with TE containing 0.3 M LiCl, the adsorbed poly (A) RNA was eluted with 2 mM EDTA (pH 7.0) containing 0.01% SDS. Using the poly (A) RNA thus obtained, single-stranded cDNA was synthesized. Specifically, 5 µg of poly (A) RNA and 0.5 µg of oligo dT primer (12–18 mer) were introduced into a sterilized 0.5 ml microcentrifuge tube, then made up to 12 µl by adding diethyl pyrocarbonate-treated sterile water and, after incubating at 70° C. for 10 minutes, immersed in ice for 1 minute. To this, 200 mM Tris-HCl (pH 8.4), 2 µl of 500 mM KCl solution, 2 µl of 25 mM $MgCl_2$, 1 µl of 10 mM dNTP and 2 µl of 0.1 M DTT were respectively added. After incubating at 42° C. for 5 minutes, there was added 1 µl comprising 200 units of Superscript II RT produced by Gibco BRL, then incubation carried out at 42° C. for a further 50 minutes, and the cDNA synthesis reaction performed. Incubation was further carried out at 70° C. for 15 minutes, the reaction terminated, and placed on ice for 5 minutes. To this reaction fluid was added 1 µl of *E. coli* RNaseH (2 units/ml) and incubation carried out at 37° C. for 20 minutes. Using as a template the cDNA obtained, on the basis of the canine IL12 base sequence (reference 16) the genes for the canine IL12 P40 subunit and P35 subunit were obtained by the PCR method and, in accordance with standard procedure, these were respectively ligated to expression vector pCDL-SRα296 (reference 17), and FOCaIL12P40 and FOCaIL12P35 obtained. 5 µg of the FOCaIL12P40 and FOCaIL12P35 were added to 4 ml of ERDF medium (produced by Kyokuto Seiyaku K. K.) containing 50 mM Tris-HCl buffer solution (pH 7.5), 400 µg/ml of DEAE dextran (produced by Pharmacia) and 100 µM chloroquine (Sigma). Meanwhile, using a 10 cm diameter dish, COS-1 cells (ATCC CRL-1650) which had been allowed to proliferate in 10% fetal bovine serum (Gibco, hereinafter abbreviated to FBS) until becoming 50% confluent were washed once with PBS, after which 4 ml of the DNA mixed solution obtained as described above was added and culture carried out under conditions comprising 5% $CO_2$ at 37° C. After 4 hours, the cells were washed with PBS and then culture carried out in 20 ml of ERDF medium under conditions comprising 5% $CO_2$ at 37° C. for 4 days, and a culture supernatant in which CaIL12 had been produced was obtained.

Example 4

Measurement of Canine IL18 Activity

Measurement of the activity of the canine IL18 produced in Example 2 was carried out as follows. Lymphocytes were isolated from canine spleen and suspended at a cell density of $10^6$ cells/ml in ERDF medium (produced by Kyokuto Seiyaku KK) containing 10% fetal bovine serum (FBS), and 2.5 ml from this and 250 U of human IL2 (produced by Genzyme) were added to a 6 cm dish. To this, 2.5 ml of respective culture supernatant obtained in Example 2 (3) was added and culturing carried out for 2 days under conditions comprising 5% $CO_2$ at 37° C. The antiviral activity of these culture fluids was measured according to the CPE method of reference 14 using vesicular stomatitis virus as the virus and MDCK (ATCC CCL-34) as the sensitive cells. As a result, when infected with recombinant virus rAcCaIG-1, approximately $10^4$ dilution units/ml of antiviral activity was detected in the culture supernatant obtained and, when infected with recombinant viruses rAcCaIG-2 and rpAcCaIGICE, at least $10^6$ dilution units/ml of antiviral activity was detected in the culture supernatants obtained. Furthermore, as a result of similarly measuring the antiviral activity of the *E. coli* and *Bombyx mori* body fluid obtained in Example 2 (1) and (5), at least $10^3$ and $10^5$ dilution units/ml of antiviral activity were detected respectively. Furthermore, using the purified canine IL18 produced by *E. coli* obtained in Example 2 (1) and the culture supernatant in which canine-IL12 was produced obtained in Example 3, the synergistic action of canine IL18 and canine IL12 in respect of their capacity for inducing this antiviral activity was investigated. A canine lymphocyte culture fluid containing human IL2 was prepared in the same way as described above, and a comparative investigation carried out of the case where there was added thereto 1 μg of purified canine IL18, the case where there was added thereto 2.5 ml of culture supernatant in which canine IL12 had been produced, and the case where there was added thereto 1 μg of purified canine IL18 and 2.5 ml of culture supernatant in which canine IL12 had been produced. As a result, there were obtained antiviral activities of approximately $10^5$ dilution units/ml with the canine IL18 on its own, approximately $3 \times 10^4$ dilution units/ml with the culture supernatant in which canine IL12 had been produced on its own, and at least $10^6$ dilution units/ml with both added. It was clear, from this, that canine IL18 and canine IL12 have a synergistic action in respect of their capacity to induce antiviral activity.

Furthermore, using cell strain FCBR1 derived from canine mammary gland tumour tissue on which class II MHC had been expressed, the class II MHC expression enhancing activity was measured in the recombinant virus-infected Sf21 cell culture fluids and *Bombyx mori* body fluid. $10^5$ FCBR1 cells were attached to 6 cm dishes and culture fluids of canine lymphocytes which had been stimulated with the aforementioned culture fluids and *Bombyx mori* body fluid were added thereto and centrifugation carried out with 1 ube under conditions comprising 5% $CO_2$ at 37° C. To the cells was added 10 μl of rat anti-canine MHC class II monoclonal antibody (produced by Serotec), further suspension in 50 μl of ERDF medium containing 10% FBS carried out and this left to stand on ice for 1 hour. After washing with PBS, suspension was carried out in 5 μl of FITC-labelled rabbit anti-rat monoclonal antibody (produced by Serotec) and 50 μl of ERDF medium containing 10% FBS, and then this was left to stand on ice for 1 hour. After washing with PBS, analysis was carried out using a Becton Dickinson FACScan. As a result, it was found that the canine IL18 produced by Sf21 cells and *Bombyx mori* stimulated the canine lymphocytes and brought about, respectively, approximately 15% and 35% increases in levels of class II MHC expression on FCBR1. It was clear, from this, that canine IL18 acts on canine lymphocytes and has activity in inducing canine IFN γ.

Next, using FCBR1 on which the Fas ligand had been expressed, Fas ligand expression enhancing activity was measured in the Sf21 cell culture fluids and *Bombyx mori* body fluid. Using rabbit anti-human Fas ligand polyclonal antibody (produced by Santa Cruz Biotechnology) and FITC-labelled mouse anti-rabbit monoclonal antibody (produced by Serotec), analysis was carried out in the same way using the FACScan. As a result, the canine IL18 produced by the Sf21 cells and *Bombyx mori* was found to have brought about, respectively, approximately 40% and 55% increases in levels of Fas ligand expression on FCBR1.

Furthermore, antitumour activity in the Sf21 cell culture fluids and *Bombyx mori* body fluid was investigated. FCBR1 cells were subjected to the action of canine IL18 produced by the Sf21 cells and *Bombyx mori*, causing intracellular DNA fragmentation and destroying cells by apoptosis. It was clear that canine IL18 exhibited direct antitumour activity towards canine tumour cells.

An investigation was also conducted into the antitumour activity of canine IL18 in vivo. When FCBR1 cells were transplanted subcutaneously in the backs of 4 week old SCID mice (obtained from Nippon Crea), it was possible to prepare 4 cancer-bearing mice in which tumours had formed. The tumour weights were calculated by means of the following equation.

Tumour weight=long diameter×short diameter$^2$/2

Two months after transplantation, when the tumour size had reached an average of 32 mm×19 mm and the tumour weights had reached 5.8 g, 10 μg of the purified canine IL18 described in Example 2 (1) produced by *E. coli* was administered twice, at a 2-day interval, into the tail veins of three of the mice. Furthermore, physiological saline was administered to one mouse at the same time as a control. After administration, the tumour weight of the control mouse increased further and, on the 10th day after administration, it had increased by 1.3-fold. On the other hand, the tumour weights of the mice to which canine IL18 had been administered decreased after administration and, in terms of the relative tumour weight with the control taken as 1, decreased to 0.05–0.1. This tumour regressing effect of canine IL18 was not inhibited by the simultaneous administration of anti-mouse interferon γ antibodies and anti-asialo GM1 antibodies. It was clear that canine IL18 also showed antitumour activity towards canine tumour cells in vivo.

Industrial Application Potential

In accordance with the present invention, IL18 can be readily mass produced. Furthermore, there can be provided canine IL18 which is effective in the treatment of canine disease.

Reference Literature

1. Wolf et.al. : J. Immunol. 146, 3074–3081 (1991)
2. Shoenhaut et al. J. Immunol. 148, 3433–3440 (1992)
3. Nastala et al. : J. Immunol. 153, 1697–1706 (1994)
4. Okamura et al. : Nature 378, 88–91 (1995)
5. Micallef et al. : Eur. J. Immunol. 26, 1647–151 (sic) (1996)
6. Ushio et al. J. Immunol. 156, 4274–4279 (1996)
7. Gu et al. : Science 275, 206–209 (1997)
8. Chirgwin et al. Biochemistry 18, 5294 (1979)
9. Berger et al. : Biochemistry 18, 5143 (1979)
10. Gubler et al. : Gene 25, 236–269 (1983)
11. Okayama et al. Mol. Cell. Biol. 2, 161 (1982) & 3, 280 (1983)
12. Horiuchi et al. : Agric. Biol. Chem. 51, 1573–1580 (1987)
13. Molecular Cloning, Cold Spring Harbour Laboratory, New York, 1982
14. Nihon Seikagakkai, Ed.: Zoku Seikagaku Jikken Koza, Vol.5, (1986), p250–256, Pub. by Tokyo Kagaku Dojin
15. Thomberry et al. : Nature 356, 768–779 (1992)
16. Okano et al. : J. Interferon and Cytokine Res. 17, 713–718 (1997)
17. Okayama et al. : Mol. Cell. Biol. 2, 161 (1982) & 3, 280 (1983)

What is claimed is:

1. An isolated protein comprising amino acids 37–193 of SEQ ID NO:2.

2. An isolated protein comprising any one of SEQ ID NO:2 or SEQ ID NO:14.

* * * * *

SEQUENCE LISTING

<160> NUMBER OF SEQ ID NOS: 14

<210> SEQ ID NO 1
<211> LENGTH: 582
<212> TYPE: DNA
<213> ORGANISM: Caninus sp.
<220> FEATURE:
<221> NAME/KEY: CDS
<222> LOCATION: (1)..(579)

<400> SEQUENCE: 1

| | | | | | | | | | | | | | | | | |
|---|---|---|---|---|---|---|---|---|---|---|---|---|---|---|---|---|
| atg | gct | act | aac | cta | ata | gaa | gac | aat | tgc | atc | aat | ctt | gtg | aaa | atg | 48 |
| Met | Ala | Thr | Asn | Leu | Ile | Glu | Asp | Asn | Cys | Ile | Asn | Leu | Val | Lys | Met | |
| 1 | | | | 5 | | | | | 10 | | | | | 15 | | |
| aaa | ttt | gtt | aac | aat | aca | ctg | tac | ttt | aaa | gcg | gaa | agt | gat | gaa | ggc | 96 |
| Lys | Phe | Val | Asn | Asn | Thr | Leu | Tyr | Phe | Lys | Ala | Glu | Ser | Asp | Glu | Gly | |
| | | | | 20 | | | | | 25 | | | | | 30 | | |
| ctg | gaa | tca | gat | tac | ttt | ggc | aag | ctt | gaa | cct | aaa | ctc | tca | atc | ata | 144 |
| Leu | Glu | Ser | Asp | Tyr | Phe | Gly | Lys | Leu | Glu | Pro | Lys | Leu | Ser | Ile | Ile | |
| | | 35 | | | | | 40 | | | | | 45 | | | | |
| cga | aat | ttg | aac | gac | caa | gtc | ctc | ttc | gtt | aac | gag | gga | aat | caa | cct | 192 |
| Arg | Asn | Leu | Asn | Asp | Gln | Val | Leu | Phe | Val | Asn | Glu | Gly | Asn | Gln | Pro | |
| | 50 | | | | | 55 | | | | | 60 | | | | | |
| gta | ttt | gag | gat | atg | ccc | gat | tct | gac | tgt | aca | gat | aat | gca | ccc | cat | 240 |
| Val | Phe | Glu | Asp | Met | Pro | Asp | Ser | Asp | Cys | Thr | Asp | Asn | Ala | Pro | His | |
| 65 | | | | | 70 | | | | | 75 | | | | | 80 | |
| acc | ata | ttt | atc | atc | tat | atg | tat | aaa | gat | agc | ctc | act | aga | ggt | ctg | 288 |
| Thr | Ile | Phe | Ile | Ile | Tyr | Met | Tyr | Lys | Asp | Ser | Leu | Thr | Arg | Gly | Leu | |
| | | | | 85 | | | | | 90 | | | | | 95 | | |
| gca | gta | act | atc | tct | gtg | aag | tat | aag | aca | atg | tct | act | ctc | tcc | tgt | 336 |
| Ala | Val | Thr | Ile | Ser | Val | Lys | Tyr | Lys | Thr | Met | Ser | Thr | Leu | Ser | Cys | |
| | | | | 100 | | | | | 105 | | | | | 110 | | |
| aag | aac | aaa | act | att | tcc | ttt | cag | aaa | atg | agt | cct | ccg | gat | agt | atc | 384 |
| Lys | Asn | Lys | Thr | Ile | Ser | Phe | Gln | Lys | Met | Ser | Pro | Pro | Asp | Ser | Ile | |
| | | 115 | | | | | 120 | | | | | 125 | | | | |
| aat | gat | gaa | gga | aat | gac | atc | ata | ttc | ttt | cag | aga | agt | gtt | cca | ggc | 432 |
| Asn | Asp | Glu | Gly | Asn | Asp | Ile | Ile | Phe | Phe | Gln | Arg | Ser | Val | Pro | Gly | |
| | 130 | | | | | 135 | | | | | 140 | | | | | |
| cat | gat | gat | aag | ata | caa | ttt | gag | tct | tca | ttg | tac | aaa | gga | cac | ttt | 480 |
| His | Asp | Asp | Lys | Ile | Gln | Phe | Glu | Ser | Ser | Leu | Tyr | Lys | Gly | His | Phe | |
| 145 | | | | | 150 | | | | | 155 | | | | | 160 | |
| cta | gct | tgt | aaa | aaa | gag | aac | gat | ctt | ttc | aaa | ctc | att | ttg | aaa | gac | 528 |
| Leu | Ala | Cys | Lys | Lys | Glu | Asn | Asp | Leu | Phe | Lys | Leu | Ile | Leu | Lys | Asp | |
| | | | | 165 | | | | | 170 | | | | | 175 | | |
| aag | gat | gaa | aat | ggg | gat | aaa | tcc | ata | atg | ttc | act | gtt | caa | aac | aag | 576 |
| Lys | Asp | Glu | Asn | Gly | Asp | Lys | Ser | Ile | Met | Phe | Thr | Val | Gln | Asn | Lys | |
| | | | | 180 | | | | | 185 | | | | | 190 | | |
| agc | tag | | | | | | | | | | | | | | | 582 |
| Ser | | | | | | | | | | | | | | | | |

<210> SEQ ID NO 2
<211> LENGTH: 193
<212> TYPE: PRT
<213> ORGANISM: Caninus sp.

<400> SEQUENCE: 2

Met Ala Thr Asn Leu Ile Glu Asp Asn Cys Ile Asn Leu Val Lys Met
 1               5                  10                  15

Lys Phe Val Asn Asn Thr Leu Tyr Phe Lys Ala Glu Ser Asp Glu Gly
             20                  25                  30

```
Leu Glu Ser Asp Tyr Phe Gly Lys Leu Glu Pro Lys Leu Ser Ile Ile
        35                  40                  45

Arg Asn Leu Asn Asp Gln Val Leu Phe Val Asn Glu Gly Asn Gln Pro
 50                  55                  60

Val Phe Glu Asp Met Pro Asp Ser Asp Cys Thr Asp Asn Ala Pro His
 65                  70                  75                  80

Thr Ile Phe Ile Ile Tyr Met Tyr Lys Asp Ser Leu Thr Arg Gly Leu
                85                  90                  95

Ala Val Thr Ile Ser Val Lys Tyr Lys Thr Met Ser Thr Leu Ser Cys
            100                 105                 110

Lys Asn Lys Thr Ile Ser Phe Gln Lys Met Ser Pro Pro Asp Ser Ile
            115                 120                 125

Asn Asp Glu Gly Asn Asp Ile Ile Phe Phe Gln Arg Ser Val Pro Gly
130                 135                 140

His Asp Asp Lys Ile Gln Phe Glu Ser Ser Leu Tyr Lys Gly His Phe
145                 150                 155                 160

Leu Ala Cys Lys Lys Glu Asn Asp Leu Phe Lys Leu Ile Leu Lys Asp
                165                 170                 175

Lys Asp Glu Asn Gly Asp Lys Ser Ile Met Phe Thr Val Gln Asn Lys
            180                 185                 190

Ser

<210> SEQ ID NO 3
<211> LENGTH: 1215
<212> TYPE: DNA
<213> ORGANISM: Caninus sp.
<220> FEATURE:
<221> NAME/KEY: CDS
<222> LOCATION: (1)..(1212)

<400> SEQUENCE: 3 atg gcc gac aag gtc ctg aag gac aag aga agg ctg ttt gtc cgg tca      48
Met Ala Asp Lys Val Leu Lys Asp Lys Arg Arg Leu Phe Val Arg Ser
 1               5                  10                  15 gta gac atg ggg acc atc aat ggt ttg ctg gat gaa ctc ttt gag aaa      96
Val Asp Met Gly Thr Ile Asn Gly Leu Leu Asp Glu Leu Phe Glu Lys
            20                  25                  30 aga gtg ctg aac cac gag gag atg gag cga gtg cgg tgt gca cac tct     144
Arg Val Leu Asn His Glu Glu Met Glu Arg Val Arg Cys Ala His Ser
        35                  40                  45 aca gtt atg gat cag gcc cga gtt ctg att gac tcc gtc ctt cgg aaa     192
Thr Val Met Asp Gln Ala Arg Val Leu Ile Asp Ser Val Leu Arg Lys
 50                  55                  60 ggg cca aat gca tgc cag att ttt att tct aat att tgc aat gag gac     240
Gly Pro Asn Ala Cys Gln Ile Phe Ile Ser Asn Ile Cys Asn Glu Asp
 65                  70                  75                  80 att cac ctg gca cag acg ctg ggg ctc tcc tca ggt tca cca tct gga     288
Ile His Leu Ala Gln Thr Leu Gly Leu Ser Ser Gly Ser Pro Ser Gly
                85                  90                  95 aat gat cat acc aaa cta gac tct caa gta gaa gtt cct tct tta cca     336
Asn Asp His Thr Lys Leu Asp Ser Gln Val Glu Val Pro Ser Leu Pro
            100                 105                 110 gcc ttc gtg gaa aac atg cct ggg cca acc att cct gac tca gaa gaa     384
Ala Phe Val Glu Asn Met Pro Gly Pro Thr Ile Pro Asp Ser Glu Glu
        115                 120                 125 tct aca gat act ctc aag ctt tgt cct cct gaa aca ttt gtg aaa atg     432
Ser Thr Asp Thr Leu Lys Leu Cys Pro Pro Glu Thr Phe Val Lys Met
130                 135                 140
```

```
tat aaa gag aag gct gaa gag atc tac cca ata aag gag aga aag gat      480
Tyr Lys Glu Lys Ala Glu Glu Ile Tyr Pro Ile Lys Glu Arg Lys Asp
145                 150                 155                 160 cgt act cgt ctg gct ctc atc ata tgc aat ata gag ttt gat cat ctt      528
Arg Thr Arg Leu Ala Leu Ile Ile Cys Asn Ile Glu Phe Asp His Leu
                165                 170                 175 tct acc agg gat gga gct gaa ctt gac att gca gga atg gag agt ctg      576
Ser Thr Arg Asp Gly Ala Glu Leu Asp Ile Ala Gly Met Glu Ser Leu
            180                 185                 190 ctg gaa ggc ctg ggc tac agt gta gtt gtg aaa cgg aaa ctc act gct      624
Leu Glu Gly Leu Gly Tyr Ser Val Val Val Lys Arg Lys Leu Thr Ala
        195                 200                 205 aag ggt atg gaa tca gtg tta cgg gaa ttt gcc gcc cgc cca gag cat      672
Lys Gly Met Glu Ser Val Leu Arg Glu Phe Ala Ala Arg Pro Glu His
    210                 215                 220 aag tcc tca gac agc aca ttc ttg gtg tta atg tct cac ggc atc ctg      720
Lys Ser Ser Asp Ser Thr Phe Leu Val Leu Met Ser His Gly Ile Leu
225                 230                 235                 240 aat gga atc tgt ggg acc gca cac agc gtg gaa gat cca gat gta cta      768
Asn Gly Ile Cys Gly Thr Ala His Ser Val Glu Asp Pro Asp Val Leu
                245                 250                 255 gct tat gac acc atc ttc cag att ttc aac aac cgt cac tgc ctc aac      816
Ala Tyr Asp Thr Ile Phe Gln Ile Phe Asn Asn Arg His Cys Leu Asn
                260                 265                 270 ctc aag gac aaa ccg aag gtc atc atc atc cag gcc tgc aga ggt gaa      864
Leu Lys Asp Lys Pro Lys Val Ile Ile Ile Gln Ala Cys Arg Gly Glu
            275                 280                 285 aat cct ggg gaa ctg tgg gtc agc gac tct cca aaa gcc tcg aca gac      912
Asn Pro Gly Glu Leu Trp Val Ser Asp Ser Pro Lys Ala Ser Thr Asp
        290                 295                 300 agc tgg aca cat caa cct ctg atg ctc aag agc gat gcc att cac aag      960
Ser Trp Thr His Gln Pro Leu Met Leu Lys Ser Asp Ala Ile His Lys
305                 310                 315                 320 gtc cac gtg gag aag gac ttc att gct ttc tgc tcc tca acc cca cat     1008
Val His Val Glu Lys Asp Phe Ile Ala Phe Cys Ser Ser Thr Pro His
                325                 330                 335 aat gtg tcc tgg aga cat atc acg aag gga tct ctt ttc att gca caa     1056
Asn Val Ser Trp Arg His Ile Thr Lys Gly Ser Leu Phe Ile Ala Gln
                340                 345                 350 ctc atc aca tgc ttc caa aaa tat tcc tgg tgc tgt cac cta gaa gga     1104
Leu Ile Thr Cys Phe Gln Lys Tyr Ser Trp Cys Cys His Leu Glu Gly
            355                 360                 365 gta ttc cgg aag gta caa caa tca ttt gaa aaa cca gat gtg aaa gcc     1152
Val Phe Arg Lys Val Gln Gln Ser Phe Glu Lys Pro Asp Val Lys Ala
        370                 375                 380 cag atg ccg acc att gaa cga gta tcc atg aca aga tat ttc tat ctc     1200
Gln Met Pro Thr Ile Glu Arg Val Ser Met Thr Arg Tyr Phe Tyr Leu
385                 390                 395                 400 ttc cct ggc aat tga                                                 1215
Phe Pro Gly Asn <210> SEQ ID NO 4
<211> LENGTH: 404
<212> TYPE: PRT
<213> ORGANISM: Caninus sp.

<400> SEQUENCE: 4

Met Ala Asp Lys Val Leu Lys Asp Lys Arg Arg Leu Phe Val Arg Ser
 1               5                  10                  15
```

-continued

```
Val Asp Met Gly Thr Ile Asn Gly Leu Leu Asp Glu Leu Phe Glu Lys
             20                  25                  30

Arg Val Leu Asn His Glu Glu Met Glu Arg Val Arg Cys Ala His Ser
         35                  40                  45

Thr Val Met Asp Gln Ala Arg Val Leu Ile Asp Ser Val Leu Arg Lys
     50                  55                  60

Gly Pro Asn Ala Cys Gln Ile Phe Ile Ser Asn Ile Cys Asn Glu Asp
 65                  70                  75                  80

Ile His Leu Ala Gln Thr Leu Gly Leu Ser Ser Gly Ser Pro Ser Gly
                 85                  90                  95

Asn Asp His Thr Lys Leu Asp Ser Gln Val Glu Val Pro Ser Leu Pro
             100                 105                 110

Ala Phe Val Glu Asn Met Pro Gly Pro Thr Ile Pro Asp Ser Glu Glu
         115                 120                 125

Ser Thr Asp Thr Leu Lys Leu Cys Pro Pro Glu Thr Phe Val Lys Met
     130                 135                 140

Tyr Lys Glu Lys Ala Glu Glu Ile Tyr Pro Ile Lys Glu Arg Lys Asp
145                 150                 155                 160

Arg Thr Arg Leu Ala Leu Ile Ile Cys Asn Ile Glu Phe Asp His Leu
                 165                 170                 175

Ser Thr Arg Asp Gly Ala Glu Leu Asp Ile Ala Gly Met Glu Ser Leu
             180                 185                 190

Leu Glu Gly Leu Gly Tyr Ser Val Val Lys Arg Lys Leu Thr Ala
         195                 200                 205

Lys Gly Met Glu Ser Val Leu Arg Glu Phe Ala Ala Arg Pro Glu His
     210                 215                 220

Lys Ser Ser Asp Ser Thr Phe Leu Val Leu Met Ser His Gly Ile Leu
225                 230                 235                 240

Asn Gly Ile Cys Gly Thr Ala His Ser Val Glu Asp Pro Asp Val Leu
                 245                 250                 255

Ala Tyr Asp Thr Ile Phe Gln Ile Phe Asn Asn Arg His Cys Leu Asn
             260                 265                 270

Leu Lys Asp Lys Pro Lys Val Ile Ile Ile Gln Ala Cys Arg Gly Glu
         275                 280                 285

Asn Pro Gly Glu Leu Trp Val Ser Asp Ser Pro Lys Ala Ser Thr Asp
     290                 295                 300

Ser Trp Thr His Gln Pro Leu Met Leu Lys Ser Asp Ala Ile His Lys
305                 310                 315                 320

Val His Val Glu Lys Asp Phe Ile Ala Phe Cys Ser Ser Thr Pro His
                 325                 330                 335

Asn Val Ser Trp Arg His Ile Thr Lys Gly Ser Leu Phe Ile Ala Gln
             340                 345                 350

Leu Ile Thr Cys Phe Gln Lys Tyr Ser Trp Cys Cys His Leu Glu Gly
         355                 360                 365

Val Phe Arg Lys Val Gln Gln Ser Phe Glu Lys Pro Asp Val Lys Ala
     370                 375                 380

Gln Met Pro Thr Ile Glu Arg Val Ser Met Thr Arg Tyr Phe Tyr Leu
385                 390                 395                 400

Phe Pro Gly Asn

<210> SEQ ID NO 5
<211> LENGTH: 1427
<212> TYPE: DNA
<213> ORGANISM: Caninus sp.
```

```
<220> FEATURE:
<221> NAME/KEY: CDS
<222> LOCATION: (251)..(829)

<400> SEQUENCE: 5
actctcaatc atacgaaatt tgaacgacca agtcctcttc gttaacgagg gaaatcaacc      60
tgtatttgag gatatgcccg attctgactg tacagataat gcaccccata ccatatttat    120
gatgctttct gcattcctgg ctgcttcagc tgccaccttt tcccatctac tcagcctcag    180 gaaagaaag agaccttaaa ccttccagat cccttcctct tataggaaac tatcgagcac      240
aggaataaag atg gct act aac cta ata gaa gac aat tgc atc aat ctt       289
           Met Ala Thr Asn Leu Ile Glu Asp Asn Cys Ile Asn Leu
               1               5                  10 gtg aaa atg aaa ttt gtt aac aat aca ctg tac ttt aaa gcg gaa agt      337
Val Lys Met Lys Phe Val Asn Asn Thr Leu Tyr Phe Lys Ala Glu Ser
    15                  20                  25 gat gaa ggc ctg gaa tca gat tac ttt ggc aag ctt gaa cct aaa ctc      385
Asp Glu Gly Leu Glu Ser Asp Tyr Phe Gly Lys Leu Glu Pro Lys Leu
30              35                  40                  45 tca atc ata cga aat ttg aac gac caa gtc ctc ttc gtt aac gag gga      433
Ser Ile Ile Arg Asn Leu Asn Asp Gln Val Leu Phe Val Asn Glu Gly
                50                  55                  60 aat caa cct gta ttt gag gat atg ccc gat tct gac tgt aca gat aat      481
Asn Gln Pro Val Phe Glu Asp Met Pro Asp Ser Asp Cys Thr Asp Asn
            65                  70                  75 gca ccc cat acc ata ttt atc atc tat atg tat aaa gat agc ctc act      529
Ala Pro His Thr Ile Phe Ile Ile Tyr Met Tyr Lys Asp Ser Leu Thr
            80                  85                  90 aga ggt ctg gca gta act atc tct gtg aag tat aag aca atg tct act      577
Arg Gly Leu Ala Val Thr Ile Ser Val Lys Tyr Lys Thr Met Ser Thr
    95                 100                 105 ctc tcc tgt aag aac aaa act att tcc ttt cag aaa atg agt cct ccg      625
Leu Ser Cys Lys Asn Lys Thr Ile Ser Phe Gln Lys Met Ser Pro Pro
110                 115                 120                 125 gat agt atc aat gat gaa gga aat gac atc ata ttc ttt cag aga agt      673
Asp Ser Ile Asn Asp Glu Gly Asn Asp Ile Ile Phe Phe Gln Arg Ser
                130                 135                 140 gtt cca ggc cat gat gat aag ata caa ttt gag tct tca ttg tac aaa      721
Val Pro Gly His Asp Asp Lys Ile Gln Phe Glu Ser Ser Leu Tyr Lys
            145                 150                 155 gga cac ttt cta gct tgt aaa aaa gag aac gat ctt ttc aaa ctc att      769
Gly His Phe Leu Ala Cys Lys Lys Glu Asn Asp Leu Phe Lys Leu Ile
            160                 165                 170 ttg aaa gac aag gat gaa aat ggg gat aaa tcc ata atg ttc act gtt      817
Leu Lys Asp Lys Asp Glu Asn Gly Asp Lys Ser Ile Met Phe Thr Val
    175                 180                 185 caa aac aag agc tagatatgaa aattgcagtt tgaattttct gagttttcgt          869
Gln Asn Lys Ser
190 ctttcagaaa aggtcataaa gagactttga gcctttaatt gtagtaatga aataaaatga    929 attatagttt caaaatatac cactaagaaa tgaataaggg gcacctgggt ggctccggca    989 gttgagcacc cgactcttaa tttcggctca tgtcatgatc tcacagttgt gggatcaagc   1049 cccacgttgg gctctgcact cagcatggga ggtaacctct ctccctctgc atctgcccct   1109 ccctccactc acacacacag gctctctctc tcttaaaatg aataattaaa atattaaaag   1169 aaaaaataaa tgaataggca ggtatcacaa aattgaaatg agtcctcctt atccaggtga   1229 ataaaatatt tgtttaacat tagaagaatg tatagtttca aaacacattc tacattgtta   1289
```

```
attgcaacat agattatatt tgtgaagtgt tcaatctttt tgggttacta gtcctaatga    1349
caaaagatac tgataactga actttctaat ttttaaaaaa tatcattaaa aacaagattt    1409
tgtaggaaaa aaaaaaaa                                                 1427
```

<210> SEQ ID NO 6
<211> LENGTH: 193
<212> TYPE: PRT
<213> ORGANISM: Caninus sp.

<400> SEQUENCE: 6

```
Met Ala Thr Asn Leu Ile Glu Asp Asn Cys Ile Asn Leu Val Lys Met
 1               5                  10                  15

Lys Phe Val Asn Asn Thr Leu Tyr Phe Lys Ala Glu Ser Asp Glu Gly
             20                  25                  30

Leu Glu Ser Asp Tyr Phe Gly Lys Leu Glu Pro Lys Leu Ser Ile Ile
         35                  40                  45

Arg Asn Leu Asn Asp Gln Val Leu Phe Val Asn Glu Gly Asn Gln Pro
     50                  55                  60

Val Phe Glu Asp Met Pro Asp Ser Asp Cys Thr Asp Asn Ala Pro His
 65                  70                  75                  80

Thr Ile Phe Ile Ile Tyr Met Tyr Lys Asp Ser Leu Thr Arg Gly Leu
                 85                  90                  95

Ala Val Thr Ile Ser Val Lys Tyr Lys Thr Met Ser Thr Leu Ser Cys
            100                 105                 110

Lys Asn Lys Thr Ile Ser Phe Gln Lys Met Ser Pro Pro Asp Ser Ile
        115                 120                 125

Asn Asp Glu Gly Asn Asp Ile Ile Phe Phe Gln Arg Ser Val Pro Gly
    130                 135                 140

His Asp Asp Lys Ile Gln Phe Glu Ser Ser Leu Tyr Lys Gly His Phe
145                 150                 155                 160

Leu Ala Cys Lys Lys Glu Asn Asp Leu Phe Lys Leu Ile Leu Lys Asp
                165                 170                 175

Lys Asp Glu Asn Gly Asp Lys Ser Ile Met Phe Thr Val Gln Asn Lys
            180                 185                 190

Ser
```

<210> SEQ ID NO 7
<211> LENGTH: 1560
<212> TYPE: DNA
<213> ORGANISM: Caninus sp.
<220> FEATURE:
<221> NAME/KEY: CDS
<222> LOCATION: (202)..(1413)

<400> SEQUENCE: 7

```
gagaaaagag tgctgaacca cgaggagatg gagcgagtgc ggtgtgcaca ctctacagtt    60
atggatcagg cccgagttct gattgactcc gtccttcgga aagggccaaa tgcatgccag   120 attttttattt ctaatatttg caatgaggac attcacctgg cacagacgct tagcacacat   180
caaggctgac agagacaaat c atg gcc gac aag gtc ctg aag gac aag aga    231
                        Met Ala Asp Lys Val Leu Lys Asp Lys Arg
                         1               5                  10 agg ctg ttt gtc cgg tca gta gac atg ggg acc atc aat ggt ttg ctg   279
Arg Leu Phe Val Arg Ser Val Asp Met Gly Thr Ile Asn Gly Leu Leu
             15                  20                  25 gat gaa ctc ttt gag aaa aga gtg ctg aac cac gag gag atg gag cga   327
```

-continued

```
                Asp Glu Leu Phe Glu Lys Arg Val Leu Asn His Glu Glu Met Glu Arg
                                30                      35                      40 gtg cgg tgt gca cac tct aca gtt atg gat cag gcc cga gtt ctg att          375
Val Arg Cys Ala His Ser Thr Val Met Asp Gln Ala Arg Val Leu Ile
            45                      50                      55 gac tcc gtc ctt cgg aaa ggg cca aat gca tgc cag att ttt att tct          423
Asp Ser Val Leu Arg Lys Gly Pro Asn Ala Cys Gln Ile Phe Ile Ser
60                      65                      70 aat att tgc aat gag gac att cac ctg gca cag acg ctg ggg ctc tcc          471
Asn Ile Cys Asn Glu Asp Ile His Leu Ala Gln Thr Leu Gly Leu Ser
75                      80                      85                      90 tca ggt tca cca tct gga aat gat cat acc aaa cta gac tct caa gta          519
Ser Gly Ser Pro Ser Gly Asn Asp His Thr Lys Leu Asp Ser Gln Val
                95                      100                     105 gaa gtt cct tct tta cca gcc ttc gtg gaa aac atg cct ggg cca acc          567
Glu Val Pro Ser Leu Pro Ala Phe Val Glu Asn Met Pro Gly Pro Thr
            110                     115                     120 att cct gac tca gaa gaa tct aca gat act ctc aag ctt tgt cct cct          615
Ile Pro Asp Ser Glu Glu Ser Thr Asp Thr Leu Lys Leu Cys Pro Pro
        125                     130                     135 gaa aca ttt gtg aaa atg tat aaa gag aag gct gaa gag atc tac cca          663
Glu Thr Phe Val Lys Met Tyr Lys Glu Lys Ala Glu Glu Ile Tyr Pro
    140                     145                     150 ata aag gag aga aag gat cgt act cgt ctg gct ctc atc ata tgc aat          711
Ile Lys Glu Arg Lys Asp Arg Thr Arg Leu Ala Leu Ile Ile Cys Asn
155                     160                     165                     170 ata gag ttt gat cat ctt tct acc agg gat gga gct gaa ctt gac att          759
Ile Glu Phe Asp His Leu Ser Thr Arg Asp Gly Ala Glu Leu Asp Ile
                175                     180                     185 gca gga atg gag agt ctg ctg gaa ggc ctg ggc tac agt gta gtt gtg          807
Ala Gly Met Glu Ser Leu Leu Glu Gly Leu Gly Tyr Ser Val Val Val
            190                     195                     200 aaa cgg aaa ctc act gct aag ggt atg gaa tca gtg tta cgg gaa ttt          855
Lys Arg Lys Leu Thr Ala Lys Gly Met Glu Ser Val Leu Arg Glu Phe
        205                     210                     215 gcc gcc cgc cca gag cat aag tcc tca gac agc aca ttc ttg gtg tta          903
Ala Ala Arg Pro Glu His Lys Ser Ser Asp Ser Thr Phe Leu Val Leu
    220                     225                     230 atg tct cac ggc atc ctg aat gga atc tgt ggg acc gca cac agc gtg          951
Met Ser His Gly Ile Leu Asn Gly Ile Cys Gly Thr Ala His Ser Val
235                     240                     245                     250 gaa gat cca gat gta cta gct tat gac acc atc ttc cag att ttc aac          999
Glu Asp Pro Asp Val Leu Ala Tyr Asp Thr Ile Phe Gln Ile Phe Asn
                255                     260                     265 aac cgt cac tgc ctc aac ctc aag gac aaa ccg aag gtc atc atc atc          1047
Asn Arg His Cys Leu Asn Leu Lys Asp Lys Pro Lys Val Ile Ile Ile
            270                     275                     280 cag gcc tgc aga ggt gaa aat cct ggg gaa ctg tgg gtc agc gac tct          1095
Gln Ala Cys Arg Gly Glu Asn Pro Gly Glu Leu Trp Val Ser Asp Ser
        285                     290                     295 cca aaa gcc tcg aca gac agc tgg aca cat caa cct ctg atg ctc aag          1143
Pro Lys Ala Ser Thr Asp Ser Trp Thr His Gln Pro Leu Met Leu Lys
    300                     305                     310 agc gat gcc att cac aag gtc cac gtg gag aag gac ttc att gct ttc          1191
Ser Asp Ala Ile His Lys Val His Val Glu Lys Asp Phe Ile Ala Phe
315                     320                     325                     330 tgc tcc tca acc cca cat aat gtg tcc tgg aga cat atc acg aag gga          1239
Cys Ser Ser Thr Pro His Asn Val Ser Trp Arg His Ile Thr Lys Gly
                335                     340                     345
```

```
tct ctt ttc att gca caa ctc atc aca tgc ttc caa aaa tat tcc tgg      1287
Ser Leu Phe Ile Ala Gln Leu Ile Thr Cys Phe Gln Lys Tyr Ser Trp
        350                 355                 360 tgc tgt cac cta gaa gga gta ttc cgg aag gta caa caa tca ttt gaa      1335
Cys Cys His Leu Glu Gly Val Phe Arg Lys Val Gln Gln Ser Phe Glu
        365                 370                 375 aaa cca gat gtg aaa gcc cag atg ccg acc att gaa cga gta tcc atg      1383
Lys Pro Asp Val Lys Ala Gln Met Pro Thr Ile Glu Arg Val Ser Met
        380                 385                 390 aca aga tat ttc tat ctc ttc cct ggc aat tgaaaagaat aagtatcaag        1433
Thr Arg Tyr Phe Tyr Leu Phe Pro Gly Asn
395                 400 agctgttagc aggcaatcat gggcagtcca gctcttcttg accaacttca aaaataccct   1493
ttgctaccat agcacactca tgtaaccttt cgtatttcaa taaaacaaa agcaaaaaaa    1553 aaaaaaa                                                             1560

<210> SEQ ID NO 8
<211> LENGTH: 404
<212> TYPE: PRT
<213> ORGANISM: Caninus sp.

<400> SEQUENCE: 8

Met Ala Asp Lys Val Leu Lys Asp Lys Arg Arg Leu Phe Val Arg Ser
 1               5                  10                  15

Val Asp Met Gly Thr Ile Asn Gly Leu Leu Asp Glu Leu Phe Glu Lys
                20                  25                  30

Arg Val Leu Asn His Glu Glu Met Glu Arg Val Arg Cys Ala His Ser
        35                  40                  45

Thr Val Met Asp Gln Ala Arg Val Leu Ile Asp Ser Val Leu Arg Lys
    50                  55                  60

Gly Pro Asn Ala Cys Gln Ile Phe Ile Ser Asn Ile Cys Asn Glu Asp
65                  70                  75                  80

Ile His Leu Ala Gln Thr Leu Gly Leu Ser Ser Gly Ser Pro Ser Gly
                85                  90                  95

Asn Asp His Thr Lys Leu Asp Ser Gln Val Glu Val Pro Ser Leu Pro
            100                 105                 110

Ala Phe Val Glu Asn Met Pro Gly Pro Thr Ile Pro Asp Ser Glu Glu
        115                 120                 125

Ser Thr Asp Thr Leu Lys Leu Cys Pro Pro Glu Thr Phe Val Lys Met
    130                 135                 140

Tyr Lys Glu Lys Ala Glu Glu Ile Tyr Pro Ile Lys Glu Arg Lys Asp
145                 150                 155                 160

Arg Thr Arg Leu Ala Leu Ile Ile Cys Asn Ile Glu Phe Asp His Leu
                165                 170                 175

Ser Thr Arg Asp Gly Ala Glu Leu Asp Ile Ala Gly Met Glu Ser Leu
            180                 185                 190

Leu Glu Gly Leu Gly Tyr Ser Val Val Lys Arg Lys Leu Thr Ala
        195                 200                 205

Lys Gly Met Glu Ser Val Leu Arg Glu Phe Ala Ala Arg Pro Glu His
    210                 215                 220

Lys Ser Ser Asp Ser Thr Phe Leu Val Leu Met Ser His Gly Ile Leu
225                 230                 235                 240

Asn Gly Ile Cys Gly Thr Ala His Ser Val Glu Asp Pro Asp Val Leu
                245                 250                 255

Ala Tyr Asp Thr Ile Phe Gln Ile Phe Asn Asn Arg His Cys Leu Asn
```

-continued

| | | 260 | | | | 265 | | | | 270 | | |
|---|---|---|---|---|---|---|---|---|---|---|---|---|

Leu Lys Asp Lys Pro Lys Val Ile Ile Gln Ala Cys Arg Gly Glu
        275              280              285

Asn Pro Gly Glu Leu Trp Val Ser Asp Ser Pro Lys Ala Ser Thr Asp
    290              295              300

Ser Trp Thr His Gln Pro Leu Met Leu Lys Ser Asp Ala Ile His Lys
305              310              315              320

Val His Val Glu Lys Asp Phe Ile Ala Phe Cys Ser Ser Thr Pro His
        325              330              335

Asn Val Ser Trp Arg His Ile Thr Lys Gly Ser Leu Phe Ile Ala Gln
            340              345            350

Leu Ile Thr Cys Phe Gln Lys Tyr Ser Trp Cys His Leu Glu Gly
        355              360            365

Val Phe Arg Lys Val Gln Gln Ser Phe Glu Lys Pro Asp Val Lys Ala
    370              375              380

Gln Met Pro Thr Ile Glu Arg Val Ser Met Thr Arg Tyr Phe Tyr Leu
385              390              395              400

Phe Pro Gly Asn

<210> SEQ ID NO 9
<211> LENGTH: 40
<212> TYPE: DNA
<213> ORGANISM: Caninus sp.

<400> SEQUENCE: 9
aactttggcc gacttcactg tacaaccgca gtaatacgga                              40

<210> SEQ ID NO 10
<211> LENGTH: 40
<212> TYPE: DNA
<213> ORGANISM: Caninus sp.

<400> SEQUENCE: 10
ccttcataca gtgaagattc aaactccatc ttgttgtgtc                              40

<210> SEQ ID NO 11
<211> LENGTH: 39
<212> TYPE: DNA
<213> ORGANISM: Caninus sp.

<400> SEQUENCE: 11
atggccgaca aggtcctgaa ggagaagaga aagctgttt                                39

<210> SEQ ID NO 12
<211> LENGTH: 39
<212> TYPE: DNA
<213> ORGANISM: Caninus sp.

<400> SEQUENCE: 12
atgtcctggg aagaggtaga acatcttgt caaagtcac                                 39

<210> SEQ ID NO 13
<211> LENGTH: 540
<212> TYPE: DNA
<213> ORGANISM: Caninus sp.
<220> FEATURE:
<221> NAME/KEY: CDS
<222> LOCATION: (1)..(537)

<400> SEQUENCE: 13

```
atg cat cct cag cag ttg gtc atc tcc tgg ttt tcc ctc gtt ttg ctg    48
Met His Pro Gln Gln Leu Val Ile Ser Trp Phe Ser Leu Val Leu Leu
 1               5                  10                  15 gcg tct ccc ctc atg gcc tac ttt ggc aag ctt gaa cct aaa ctc tca    96
Ala Ser Pro Leu Met Ala Tyr Phe Gly Lys Leu Glu Pro Lys Leu Ser
             20                  25                  30 atc ata cga aat ttg aac gac caa gtc ctc ttc gtt aac gag gga aat   144
Ile Ile Arg Asn Leu Asn Asp Gln Val Leu Phe Val Asn Glu Gly Asn
         35                  40                  45 caa cct gta ttt gag gat atg ccc gat tct gac tgt aca gat aat gca   192
Gln Pro Val Phe Glu Asp Met Pro Asp Ser Asp Cys Thr Asp Asn Ala
     50                  55                  60 ccc cat acc ata ttt atc atc tat atg tat aaa gat agc ctc act aga   240
Pro His Thr Ile Phe Ile Ile Tyr Met Tyr Lys Asp Ser Leu Thr Arg
 65                  70                  75                  80 ggt ctg gca gta act atc tct gtg aag tat aag aca atg tct act ctc   288
Gly Leu Ala Val Thr Ile Ser Val Lys Tyr Lys Thr Met Ser Thr Leu
                 85                  90                  95 tcc tgt aag aac aaa act att tcc ttt cag aaa atg agt cct ccg gat   336
Ser Cys Lys Asn Lys Thr Ile Ser Phe Gln Lys Met Ser Pro Pro Asp
            100                 105                 110 agt atc aat gat gaa gga aat gac atc ata ttc ttt cag aga agt gtt   384
Ser Ile Asn Asp Glu Gly Asn Asp Ile Ile Phe Phe Gln Arg Ser Val
        115                 120                 125 cca ggc cat gat gat aag ata caa ttt gag tct tca ttg tac aaa gga   432
Pro Gly His Asp Asp Lys Ile Gln Phe Glu Ser Ser Leu Tyr Lys Gly
    130                 135                 140 cac ttt cta gct tgt aaa aaa gag aac gat ctt ttc aaa ctc att ttg   480
His Phe Leu Ala Cys Lys Lys Glu Asn Asp Leu Phe Lys Leu Ile Leu
145                 150                 155                 160 aaa gac aag gat gaa aat ggg gat aaa tcc ata atg ttc act gtt caa   528
Lys Asp Lys Asp Glu Asn Gly Asp Lys Ser Ile Met Phe Thr Val Gln
                165                 170                 175 aac aag agc tag                                                   540
Asn Lys Ser
```

<210> SEQ ID NO 14
<211> LENGTH: 179
<212> TYPE: PRT
<213> ORGANISM: Caninus sp.

<400> SEQUENCE: 14

```
Met His Pro Gln Gln Leu Val Ile Ser Trp Phe Ser Leu Val Leu Leu
 1               5                  10                  15

Ala Ser Pro Leu Met Ala Tyr Phe Gly Lys Leu Glu Pro Lys Leu Ser
             20                  25                  30

Ile Ile Arg Asn Leu Asn Asp Gln Val Leu Phe Val Asn Glu Gly Asn
         35                  40                  45

Gln Pro Val Phe Glu Asp Met Pro Asp Ser Asp Cys Thr Asp Asn Ala
     50                  55                  60

Pro His Thr Ile Phe Ile Ile Tyr Met Tyr Lys Asp Ser Leu Thr Arg
 65                  70                  75                  80

Gly Leu Ala Val Thr Ile Ser Val Lys Tyr Lys Thr Met Ser Thr Leu
                 85                  90                  95

Ser Cys Lys Asn Lys Thr Ile Ser Phe Gln Lys Met Ser Pro Pro Asp
            100                 105                 110

Ser Ile Asn Asp Glu Gly Asn Asp Ile Ile Phe Phe Gln Arg Ser Val
        115                 120                 125
```

```
Pro Gly His Asp Asp Lys Ile Gln Phe Glu Ser Ser Leu Tyr Lys Gly
    130                 135                 140

His Phe Leu Ala Cys Lys Lys Glu Asn Asp Leu Phe Lys Leu Ile Leu
145                 150                 155                 160

Lys Asp Lys Asp Glu Asn Gly Asp Lys Ser Ile Met Phe Thr Val Gln
                165                 170                 175

Asn Lys Ser
```